(12) United States Patent
Choi et al.

(10) Patent No.: US 7,879,463 B2
(45) Date of Patent: *Feb. 1, 2011

(54) DIMETHYLENECYCLOHEXANE COMPOUND, METHOD OF PREPARING THE SAME AND ORGANIC LIGHT EMITTING DEVICE COMPRISING THE DIMETHYLENECYCLOHEXANE COMPOUND

(75) Inventors: Byoung-Ki Choi, Yongin-si (KR);
O-Hyun Kwon, Yongin-si (KR);
Che-Un Yang, Yongin-si (KR);
Woon-Jung Paek, Yongin-si (KR);
Myeong-Suk Kim, Yongin-si (KR);
Dong-Woo Shin, Yongin-si (KR);
Eun-Sil Han, Yongin-si (KR); Yi-Yeol Lyu, Yongin-si (KR); Sang-Hoon Park, Yongin-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 719 days.

This patent is subject to a terminal disclaimer.

(21) Appl. No.: 11/798,171

(22) Filed: May 10, 2007

(65) Prior Publication Data
US 2007/0264526 A1 Nov. 15, 2007

(30) Foreign Application Priority Data
May 10, 2006 (KR) .................. 10-2006-0041970
Dec. 18, 2006 (KR) .................. 10-2006-0129657

(51) Int. Cl.
*H01L 51/54* (2006.01)
*C09K 11/06* (2006.01)
(52) U.S. Cl. ............... 428/690; 428/917; 313/504; 313/506; 257/40; 257/E51.049; 257/E51.051; 564/427; 564/434; 585/26
(58) Field of Classification Search .............. None
See application file for complete search history.

(56) References Cited

U.S. PATENT DOCUMENTS

| 4,356,429 | A | 10/1982 | Tang |
| 5,759,444 | A | 6/1998 | Enokida et al. ........ 252/301.16 |

| 2001/0043043 | A1* | 11/2001 | Aoyama et al. .......... 313/506 |
| 2006/0068221 | A1* | 3/2006 | Saitoh et al. ............ 428/690 |
| 2007/0026258 | A1* | 2/2007 | Choi et al. ............... 428/690 |

FOREIGN PATENT DOCUMENTS

| JP | 11-003782 | | 1/1999 |
| JP | 11-329734 | | 11/1999 |
| JP | 2003-186214 | | 7/2003 |
| JP | 2003270811 | A * | 9/2003 |
| JP | 2005047811 | A * | 2/2005 |

OTHER PUBLICATIONS

Machine translation of JP2003-270811. Date of publication: Sep. 25, 2003.*
Machine translation of JP2005-047811. Date of publication: Feb. 24, 2005.*
Yoshiyuki Kuwabara et al., "Thermally Stable Multilayered Organic Electrolunimescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials", Adv. Mater. 1994, 6, No. 9, pp. 677-679.
Machine translation of JP 2003-186214 into English.
Office Action (Paper No. 20091230) issued by U.S. PTO on Jan. 8, 2010 in U.S. Appl. No. 11/493,839.

* cited by examiner

*Primary Examiner*—D. Lawrence Tarazano
*Assistant Examiner*—Andrew K Bohaty
(74) *Attorney, Agent, or Firm*—Robert E. Bushnell, Esq.

(57) ABSTRACT

Provided are a dimethylenecyclohexane compound represented by Formula 1 below, a method of preparing the same and an organic light emitting device comprising the dimethylenecyclohexane compound:

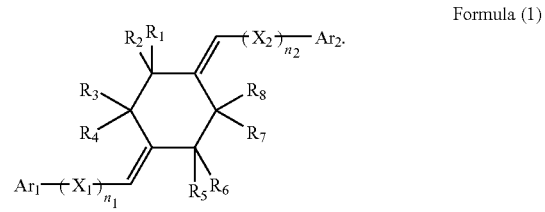

Formula (1)

The organic light emitting device comprising the dimethylenecyclohexane compound represented by Formula 1 has a low driving voltage, excellent efficiency and improved color purity.

20 Claims, 1 Drawing Sheet

FIG. 1A

| | |
|---|---|
| SECOND ELECTRODE | 111 |
| ELECTRON INJECTION LAYER | 109 |
| ELECTRON TRANSPORT LAYER | 107 |
| EMISSIVE LAYER | 105 |
| HOLE INJECTION LAYER | 103 |
| FIRST ELECTRODE | 101 |

FIG. 1B

| | |
|---|---|
| SECOND ELECTRODE | 111 |
| ELECTRON INJECTION LAYER | 109 |
| ELECTRON TRANSPORT LAYER | 107 |
| EMISSIVE LAYER | 105 |
| HOLE TRANSPORT LAYER | 104 |
| HOLE INJECTION LAYER | 103 |
| FIRST ELECTRODE | 101 |

FIG. 1C

| | |
|---|---|
| SECOND ELECTRODE | 111 |
| ELECTRON INJECTION LAYER | 109 |
| ELECTRON TRANSPORT LAYER | 107 |
| HOLE BLOCKING LAYER | 106 |
| EMISSIVE LAYER | 105 |
| HOLE TRANSPORT LAYER | 104 |
| HOLE INJECTION LAYER | 103 |
| FIRST ELECTRODE | 101 |

DIMETHYLENECYCLOHEXANE COMPOUND, METHOD OF PREPARING THE SAME AND ORGANIC LIGHT EMITTING DEVICE COMPRISING THE DIMETHYLENECYCLOHEXANE COMPOUND

CROSS-REFERENCE TO RELATED PATENT APPLICATION AND CLAIM OF PRIORITY

This application claims the benefit of Korean Patent Application Nos. 10-2006-0041970, filed on May 10, 2006 and 10-2006-0129657, filed on Dec. 18, 2006 in the Korean Intellectual Property Office, the disclosure of which is incorporated herein in its entirety by reference.

BACKGROUND OF THE INVENTION

1. Field of the Invention

The present invention relates to a dimethylenecyclohexane compound, a method of preparing the same, and an organic light emitting device comprising the dimethylenecyclohexane compound, and more particularly, to a dimethylenecyclohexane compound which has excellent electrical properties, thermal stability and photochemical stability such that an organic light emitting device comprising the dimethylenecyclohexane compound has a low driving voltage, and excellent efficiency and color purity, a method of preparing the dimethylenecyclohexane compound, and an organic light emitting device including an organic layer comprising the dimethylenecyclohexane compound.

2. Description of the Related Art

Light emitting devices, which are self-emitting devices, have wide viewing angles, excellent contrast, and quick response. Light emitting devices can be classified as inorganic light emitting devices, which include emitting layers formed of an inorganic compound, and organic light emitting devices, which include emitting layers formed of an organic compound. Organic light emitting devices are brighter, and have a lower operating voltage and quicker response compared to inorganic light emitting devices. Furthermore, organic light emitting devices can realize multi colors. Due to these advantages of organic light emitting devices, extensive research into organic light emitting devices has been conducted.

Typically, an organic light emitting device has an anode/organic emissive layer/cathode structure. An organic light emitting device can also have various other structures, such as an anode/hole injection layer/hole transport layer/emissive layer/electron transport layer/electron injection layer/cathode structure or an anode/hole injection layer/hole transport layer/emissive layer/hole blocking layer/electron transport layer/electron injection layer/cathode structure.

A material that is used to form the emissive layer or the hole injection layer can be, for example, an anthracene substituted by two naphthyl groups disclosed in Japanese Patent Laid-Open Publication No. 1999-003782. However, the driving voltage, efficiency and color purity of an organic light emitting device using such a conventional compound do not meet desired levels. Accordingly, a material is required that can improve the driving voltage, efficiency and color purity of an organic light emitting device.

SUMMARY OF THE INVENTION

The present invention provides a dimethylenecyclohexane compound that can improve the driving voltage, efficiency and color purity of an organic light emitting device.

The present invention also provides a method of preparing the dimethylenecyclohexane compound.

The present invention also provides an organic light emitting device including the dimethylenecyclohexane compound.

According to an aspect of the present invention, there is provided a dimethylenecyclohexane compound represented by Formula 1 below:

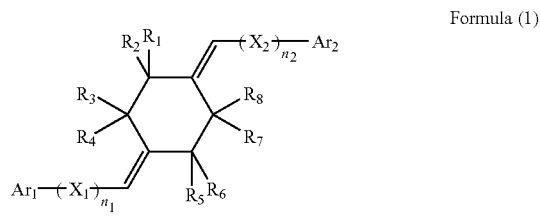

Formula (1)

where $R_1$, $R_2$, $R_3$, $R_4$, $R_5$, $R_6$, $R_7$ and $R_8$ may each independently be a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group represented by —N(Z')(Z"). Z' and Z" are each independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group;

each of $X_1$ and $X_2$ is independently a single bond, a double bond, a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_1$-$C_{20}$ heteroalkylene group, a substituted or unsubstituted $C_7$-$C_{30}$ alkylenearylene group, a substituted or unsubstituted $C_6$-$C_{30}$ arylene group, or a substituted or unsubstituted $C_2$-$C_{30}$ heteroarylene group;

$n_1$ and $n_2$ may each independently be an integer in the range of 0 to 5, and when $n_1$ or $n_2$ is 2 or greater, the $X_1$s or $X_2$s can be respectively identical or different;

$Ar_1$ and $Ar_2$ may each independently be a substituted or unsubstituted $C_6$-$C_{30}$ aryl group, a substituted or unsubstituted $C_2$-$C_{30}$ heteroaryl group, a substituted or unsubstituted $C_4$-$C_{30}$ cycloalkyl group or a substituted or unsubstituted $C_2$-$C_{30}$ cycloheteroalkyl group; and at least one of $Ar_1$ and $Ar_2$ includes at least two substituents, the at least two substituents included in $Ar_1$ or $Ar_2$ are each independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or a substituted amino group represented by —N(R')(R"), where R' and R" are each independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a $C_5$-$C_{20}$ cycloalkyl group, or a $C_5$-$C_{30}$ heterocycloalkyl group.

According to another aspect of the present invention, there is provided a method of preparing the dimethylenecyclohexane compound represented by Formula 1 comprising: reacting the compound represented by Formula 1A with the compound represented by Formula 1B and the compound represented by Formula 1C to obtain the compound represented by Formula 1D; and reacting the compound represented by Formula 1D with compounds including at least one of (1) a compound represented by Formula 1E and the compound represented by 1F, and (2) a compound represented by Formula 1G and a compound represented by Formula 1H to obtain the compound represented by Formula 1:

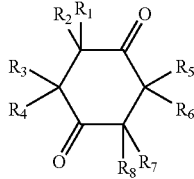
Formula (1A)

$m_1Ha_1\text{-}Ar_2'\text{-}(X_2)_{\overline{n_1}}PO(OEt)_2$  Formula (1B)

$m_2Ha_2\text{-}Ar_2'\text{-}(X_2)_{\overline{n_2}}PO(OEt)_2$  Formula (1C)

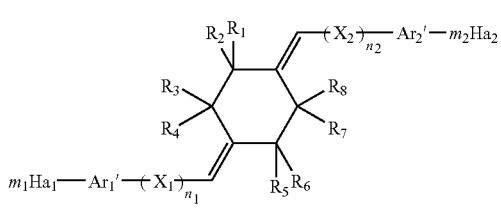
Formula (1D)

$L_1\text{-}Q_1$  Formula (1E)

$L_2\text{-}Q_2$  Formula (1F)

$L_3\text{-}Q_3$  Formula (1G)

$L_4\text{-}Q_4$  Formula (1H)

where $R_1$, $R_2$, $R_3$, $R_4$, $R_5$, $R_6$, $R_7$, $R_8$, $X_1$, $X_2$, $n_1$ and $n_2$ are the same as defined in Formula 1;

each of $Ar_1$ and $Ar_2$ is independently a substituted or unsubstituted $C_6$-$C_{30}$ aryl group, a substituted or unsubstituted $C_2$-$C_{30}$ heteroaryl group, a substituted or unsubstituted $C_4$-$C_{30}$ cycloalkyl group or a substituted or unsubstituted $C_2$-$C_{30}$ cycloheteroalkyl group;

each of $Ha_1$ and $Ha_2$ is a halogen atom;

each of $m_1$ and $m_2$ is an integer in the range of 0 to 5, and at least either one of $m_1$ and $m_2$ is an integer of 1 or more;

Formula 1B and Formula 1C are the same or different from each other;

$L_1$, $L_2$, $L_3$ and $L_4$ are each independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or a substituted amino group represented by —N(R')(R") where each of R' and R" is independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group; and each of $Q_1$, $Q_2$, $Q_3$ and $Q_4$ is independently a B-containing group or H when $L_1$, $L_2$, $L_3$ and $L_4$ are the substituted amino groups represented by —N(R')(R"), $L_1$ and $L_2$ are substituents included in $Ar_1$, and $L_3$ and $L_4$ are substituents included in $Ar_2$. Q1, Q2, Q3 and Q4 may be the same or different, and L1, L2, L3 and L4 may be the same or different.

According to another aspect of the present invention, there is provided an organic light emitting device comprising a first electrode; a second electrode; and at least one organic layer disposed between the first electrode and the second electrode, wherein the organic layer comprises the dimethylenecyclohexane compound represented by Formula 1 as described above.

The dimethylenecyclohexane compound represented by Formula 1 has excellent thermal stability, photochemical stability and optical property, and an organic light emitting device comprising the same has a low driving voltage, excellent efficiency and improved color purity.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein:

FIGS. 1A through 1C are schematic cross-sectional views of organic light emitting devices according to embodiments of the present invention.

DETAILED DESCRIPTION OF THE INVENTION

Hereinafter, the present invention will be described more fully with reference to the accompanying drawings, in which exemplary embodiments of the invention are shown.

A dimethylenecyclohexane compound according to an embodiment of the present invention is represented by Formula 1 below:

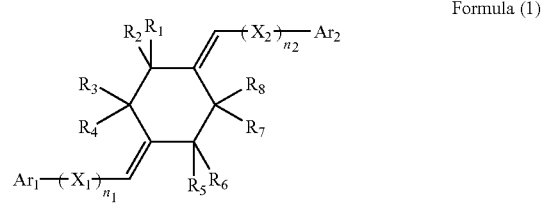
Formula (1)

where the two double bonds and the dimethylenecyclohexane group connected to the two double bonds increase the solubility of the dimethylenecyclohexane compound represented by Formula 1, and the $Ar_1$—$(X_1)_{n1}$— and $Ar_2$—$(X_2)_{n2}$— improve the film proccessibility, quantum yield, thermal stability, photo chemical stability and photoluminescence (PL) properties of the dimethylenecyclohexane compound represented by Formula 1, due to substituents included in $Ar_1$ and/or $Ar_2$. Accordingly, the dimethylenecyclohexane compound represented by Formula 1 is suitable for a material forming an organic layer interposed between first and second electrodes in an organic light emitting device. The dimethylenecyclohexane compound represented by Formula 1 is suitable for an organic layer, in particular, a hole injection layer, a hole transport layer or an emissive layer.

In Formula 1, $R_1$, $R_2$, $R_3$, $R_4$, $R_5$, $R_6$, $R_7$ and $R_8$ may each independently be a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group having —N(Z')(Z"). Z' and Z" are each independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group.

In the current embodiment, when at least one hydrogen atom included in the alkyl group, the alkoxy group, the aryl group, the heteroaryl group, the cycloalkyl group or the heterocycloalkyl group is substituted, the substituents may each independently be at least one selected from the group consisting of —F, —Cl, —Br, —CN, —NO$_2$, —OH; a $C_1$-$C_{20}$ alkyl group that is unsubstituted or substituted with —F, —Cl, —Br, —CN, —NO$_2$ or —OH; a $C_1$-$C_{20}$ alkoxy group that is unsubstituted or substituted with —F, —Cl, —Br, —CN, —NO$_2$ or —OH; a $C_6$-$C_{30}$ aryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_2$-$C_{30}$ heteroaryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_5$-$C_{20}$ cycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH; and a $C_5$-$C_{30}$ heterocycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH.

In Formula 1, each of $X_1$ and $X_2$ is independently a single bond, a double bond, a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_1$-$C_{20}$ heteroalkylene group, a substituted or unsubstituted $C_7$-$C_{30}$ alkylenearylene group, a substituted or unsubstituted $C_6$-$C_{30}$ arylene group, a substituted or unsubstituted $C_2$-$C_{30}$ heteroarylene group.

The alkylene group represents a branched or straight bivalent alkylene group, and the heteroalkylene group represents that at least one carbon atom existing in the alkylene group is substituted with N, O, S, or P.

The arylene group is a bivalent group having aromatic rings, 2 or more of which can be bound to or fused with each other. The heteroarylene group is a bivalent group having aromatic rings substituted with at least one of N, O, S and P in at least one carbon atom of the arylene groups.

When at least one hydrogen atom included in the alkylene group, the heteroalkylene group, the arylene group or the heteroarylene group is substituted, the substituents may each independently be at least one selected from the group consisting of —F, —Cl, —Br, —CN, —NO$_2$, —OH; a $C_1$-$C_{20}$ alkyl group that is unsubstituted or substituted with —F, —Cl, —Br, —CN, —NO$_2$ or —OH; a $C_1$-$C_{20}$ alkoxy group that is unsubstituted or substituted with —F, —Cl, —Br, —CN, —NO$_2$ or —OH; a $C_6$-$C_{30}$ aryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_2$-$C_{30}$ heteroaryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_5$-$C_{20}$ cycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH; and a $C_5$-$C_{30}$ heterocycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH.

In particular, in Formula 1, $X_1$ and $X_2$ may each independently be one of a single bond, a methylene group, an ethylene group, a —O— methylene group, a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluoromethoxyphenylene group, an o-, m-, or p-tolylene group, an o-, m- or p-cumenylene group, a mesitylene group, a phenoxyphenylene group, a (α,α-dimethylbenzene)phenylene group, a (N,N'-dimethyl)aminophenylene group, a (N,N'-diphenyl)aminophenylene group, a ($C_1$-$C_{10}$ alkylcyclohexyl)phenylene group, a (anthracenyl)phenylene group, a pentalenylene group, an indenylene group, a naphthylene group, a $C_1$-$C_{10}$ alkylnaphthylene group, a $C_1$-$C_{10}$ alkoxynaphthylene group, a halonaphthylene group, a cyanonaphthylene group, a biphenylenylene group, a $C_1$-$C_{10}$ alkyl biphenylenylene group, a $C_1$-$C_{10}$ alkoxy biphenylenylene group, an anthracenylene group, an azulenylene group, a heptalenylene group, an acenaphthylenylene group, a phenalenylene group, a fluorenylene group, a methylanthrylene group, a phenanthrenylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylenylene group, a hexaphenylene group, a hexacenylene group, a rubicenylene group, a coronenylene group, a trinaphthylenylene group, a heptaphenylene group, a heptacenylene group, a pyranthrenylene group, an ovalenylene group, a carbazolylene group, a $C_{1-10}$ alkyl carbazolylene group, a thiophenylene group, an indolylene group, a purinylene group, a benzimidazolylene group, a quinolinylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridinylene group, a pyridazinylene group, a pyrimidinylene group, a pyrazinylene group, and a thianthrenylene group. However, $X_1$ and $X_2$ are not limited to these groups.

Among the above examples, $X_1$ and $X_2$ may be a single bond, a phenylene group or an anthracenylene group.

$X_1$ and $X_2$ can be different or identical, and preferably identical.

In Formula 1, $n_1$ and $n_2$ are respectively the repeating number of $X_1$ and $X_2$. $n_1$ and $n_2$ may each independently be an integer in the range of 0 to 5, and preferably, in the range of 0 to 3.

When $n_1$ is 2 or greater, the $X_1$s can be identical or different and when $n_2$ is 2 or greater, the $X_2$s can be identical or different.

In Formula 1, $Ar_1$ and $Ar_2$ may be each independently a substituted or unsubstituted $C_6$-$C_{30}$ aryl group, a substituted or unsubstituted $C_2$-$C_{30}$ heteroaryl group, a substituted or unsubstituted $C_4$-$C_{30}$ cycloalkyl group or a substituted or unsubstituted $C_2$-$C_{30}$ cycloheteroalkyl group, and at least one of $Ar_1$ and $Ar_2$ includes at least two substituents. At least two substituents included in $Ar_1$ include $L_1$ and $L_2$, and at least two substituents included in $Ar_2$ include $L_3$ and $L_4$.

$L_1$, $L_2$, $L_3$, and $L_4$ may each independently be a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group or a substituted amino group represented by —N(R')(R") where R' and R" may each independently be a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a $C_5$-$C_{20}$ cycloalkyl group, a $C_5$-$C_{30}$ heterocycloalkyl group.

The aryl group is a monovalent group having aromatic rings, 2 or more of which can be bound to or fused with each other. The heteroaryl group is a group having aromatic rings substituted with at least one of N, O, S and P in at least one carbon atom of the aryl groups. The cycloalkyl group is an alkyl group having a ring and the heterocycloalkyl group is a group substituted with at least one of N, O, S and P in at least one carbon atom of the cycloalkyl group.

When at least one hydrogen atom included in the aryl group, the heteroaryl group, the cycloalkyl group and the heterocycloalkyl group is substituted, the substituents may each independently include at least one of —F; —Cl; —Br; —CN; —NO$_2$; —OH; a $C_1$-$C_{20}$ alkyl group that is unsubstituted or substituted with —F, —Cl, —Br, —CN, —NO$_2$ or —OH; a $C_1$-$C_{20}$ alkoxy group that is unsubstituted or substituted with —F, —Cl, —Br, —CN, —NO$_2$ or —OH; a $C_6$-$C_{30}$ aryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_2$-$C_{30}$ heteroaryl group that is unsubstituted or substituted with a $C_1$-$C_{20}$ alkyl group, a $C_1$-$C_{20}$ alkoxy group, —F, —Cl, —Br, —CN, —NO$_2$ or —OH; a $C_5$-$C_{20}$ cycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH; and a $C_5$-$C_{30}$ heterocycloalkyl group that is unsubstituted or substituted with a $C_1$-$C_{20}$ alkyl group, a $C_1$-$C_{20}$ alkoxy group, —F, —Cl, —Br, —CN, —NO$_2$ or —OH.

In particular, in Formula 1, $L_1$, $L_2$, $L_3$, and $L_4$ may each independently be one of a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a ($C_1$-$C_{10}$ alkylcyclohexyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenylenyl group, a $C_1$-$C_{10}$ alkoxy biphenylenyl group, an anthracenyl group, a $C_1$-$C_{10}$ alkyl anthracenyl group, a $C_1$-$C_{10}$ alkoxy anthracenyl group, an azulenyl group, a heptalenyl group, an acenaphthylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a $C_1$-$C_{10}$ alkyl carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, a $C_1$-$C_{10}$ alkylcyclohexyl group, a $C_1$-$C_{10}$ alkoxycyclohexyl group, an oxyranyl group, a pyrrolidinyl group, a pyrazolidinyl group, an imidazolidinyl group, a piperidinyl group, a piperazinyl group, a morpholinyl group, 9,9-diphenyl-9H-fluorene-2-yl, a spirofluorenyl group and an amino group represented by —N(R')(R") where R' and R" may each independently be one of a hydrogen atom, a phenyl group, a $C_1$-$C_{10}$ alkyl phenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a ($C_1$-$C_{10}$ alkylcyclohexyl)phenyl group, an anthracenyl phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group and a $C_1$-$C_{10}$ alkyl biphenylenyl group. However, R' and R" are not limited to these groups, and $L_1$, $L_2$, $L_3$, and $L_4$ are not limited to these groups.

Among the above groups, $L_1$, $L_2$, $L_3$, and $L_4$, may each independently be one of a carbazole group, a phenyl group, a naphthyl group, an anthracenyl group, or N(R')(R") in which R' and R" are each independently a naphthyl group or a phenyl group, and more preferably, a carbazole group.

An exemplary example of the dimethylenecyclohexane compound of Formula 1 includes a compound represented by Formula 2 below:

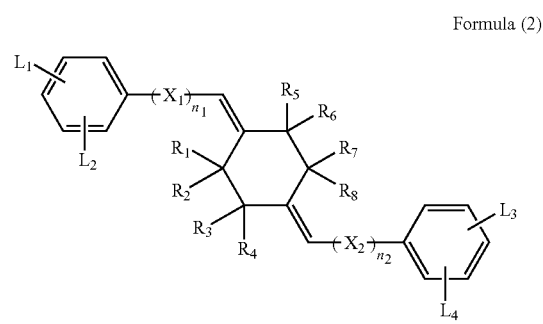

Formula (2)

where $R_1$, $R_2$, $R_3$, $R_4$, $R_5$, $R_6$, $R_7$, $R_8$, $X_1$, $X_2$, $n_1$, $n_2$, $L_1$, $L_2$, $L_3$ and $L_4$ are the same as defined in Formula 1.

A more exemplary example of the dimethylenecyclohexane compound of Formula 2 includes compounds represented by Formula 3 or 4.

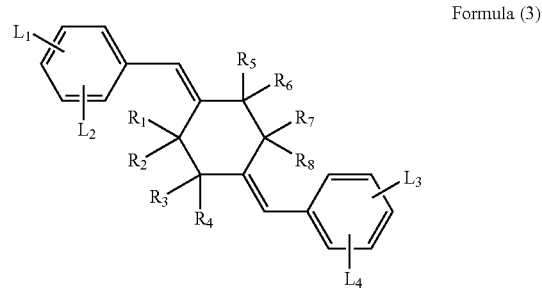

Formula (3)

where $R_1$, $R_2$, $R_3$, $R_4$, $R_5$, $R_6$, $R_7$, $R_8$, $L_1$, $L_2$, $L_3$ and $L_4$ are the same as defined in Formula 1.

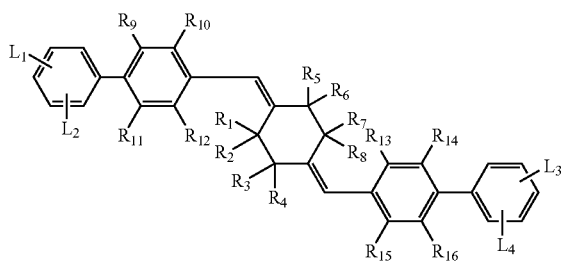

Formula (4)

where $R_1$, $R_2$, $R_3$, $R_4$, $R_5$, $R_6$, $R_7$, $R_8$, $L_1$, $L_2$, $L_3$ and $L_4$ are the same as defined in Formula 1; each of $R_9$, $R_{10}$, $R_{11}$, $R_{12}$, $R_{13}$, $R_{14}$, $R_{15}$, and $R_{16}$ is independently hydrogen, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group represented by —N(Z')(Z''); and each of Z' and Z'' is independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group.

According to an embodiment of the present invention, the dimethylenecyclohexane compound of Formula 1 can be represented by one of Formulae 5 through 8 below, but is not limited thereto:

Formula 5

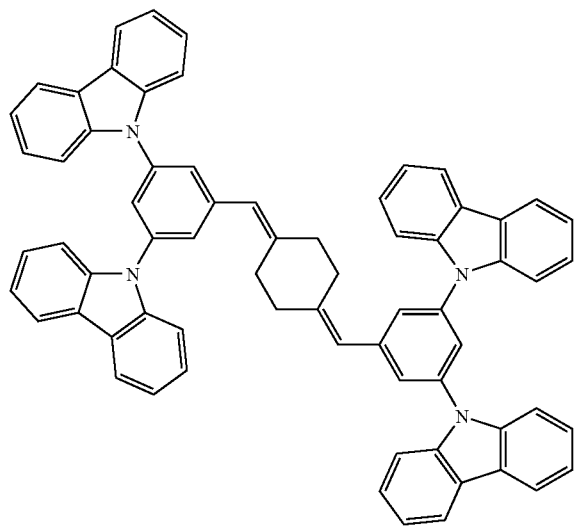

Formula 6

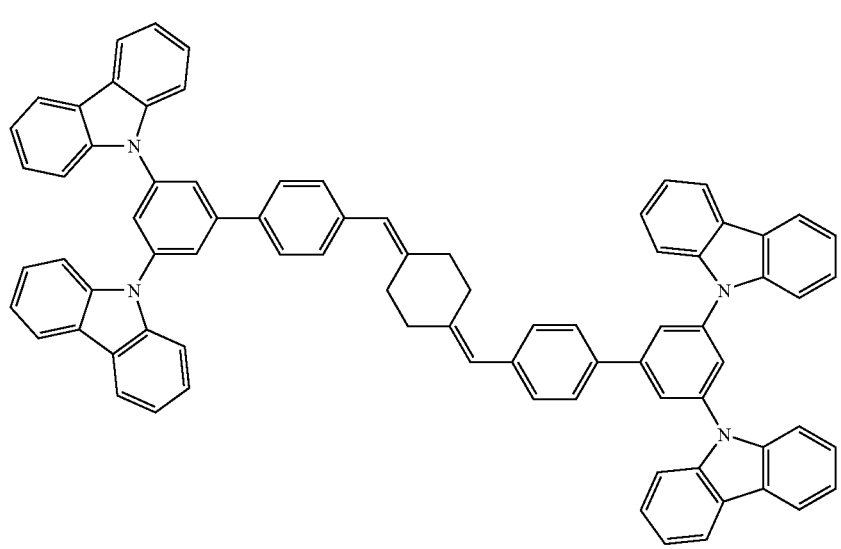

-continued

Formula 7

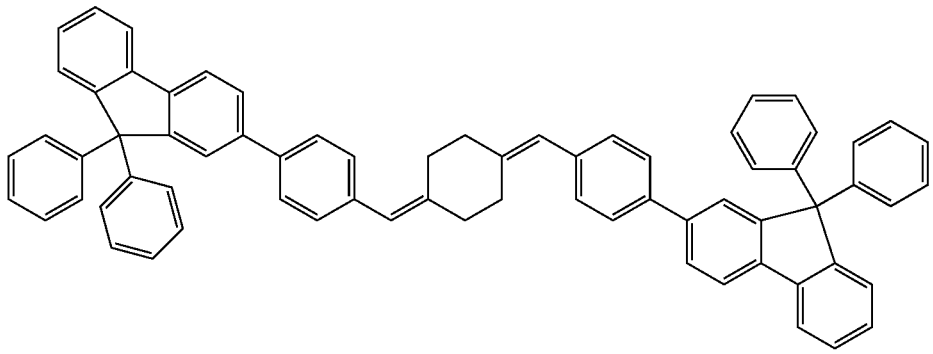

Formula 8

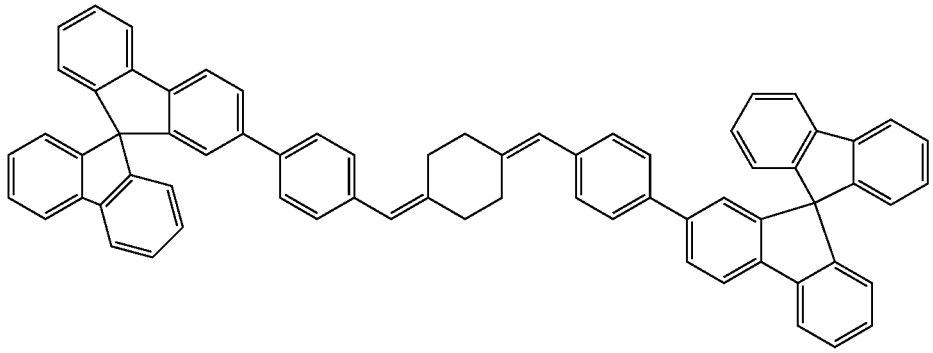

The dimethylenecyclohexane compound represented by Formula 1 can be synthesized using a conventional organic synthesis method. A method of preparing the dimethylenecyclohexane compound represented by Formula 1 according to an embodiment of the present invention includes reacting a compound represented by Formula 1A with the compound represented by Formula 1B and the compound represented by Formula 1C to obtain a compound represented by Formula 1D, and reacting the compound represented by Formula 1D with compounds including at least one of (1) a compound represented by Formula 1E, and a compound represented by Formula 1F, and (2) a compound represented by Formula 1G, and a compound represented by Formula 1H to obtain the dimethylenecyclohexane compound represented by Formula 1:

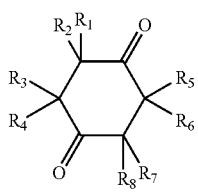

Formula (1A)

$m_1Ha_1\text{-}Ar_1\text{'}\text{-}(X_1)_{\overline{n_1}}PO(OEt)_2$  Formula (1B)

$m_2Ha_2\text{-}Ar_2\text{'}\text{-}(X_2)_{\overline{n_2}}PO(OEt)_2$  Formula (1C)

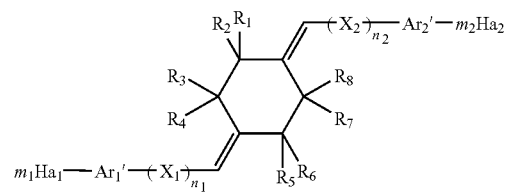

Formula (1D)

$L_1\text{-}Q_1$  Formula (1E)

$L_2\text{-}Q_2$  Formula (1F)

$L_3\text{-}Q_3$  Formula (1G)

$L_4\text{-}Q_4$  Formula (1H)

where $R_1$, $R_2$, $R_3$, $R_4$, $R_5$, $R_6$, $R_7$, $R_8$, $X_1$, $X_2$, $n_1$, and $n_2$ are the same as defined in Formula 1;

$Ar_1$' and $Ar_2$' are each independently a substituted or unsubstituted $C_6$-$C_{30}$ aryl group, a substituted or unsubstituted $C_2$-$C_{30}$ heteroaryl group, a substituted or unsubstituted $C_4$-$C_{30}$ cycloalkyl group or a substituted or unsubstituted $C_2$-$C_{30}$ cycloheteroalkyl group;

In Formulae 1B and 1C, each of $Ha_1$ and $Ha_2$ is independently a halogen group such as F, Cl, Br or I, and preferably, Br; and Each of $m_1$ and $m_2$ is an integer in the range of 0 to 5, wherein either $m_1$ or $m_2$ is an integer of 1 or more.

Formula 1B and Formula 1C may be the same or different from each other.

In Formulae $L_1$-$Q_1$, $L_2$-$Q_2$, $L_3$-$Q_3$, and $L_4$-$Q_4$, $L_1$, $L_2$, $L_3$ and $L_4$ are the same as defined in Formula 1, wherein $Q_1$, $Q_2$, $Q_3$, and $Q_4$ are each independently a B-containing group, or H when $L_1$, $L_2$, $L_3$ and $L_4$ are substituted amino groups represented by —N(R')(R''). Q1, Q2, Q3 and Q4 may be different or identical, and L1, L2, L3 and L4 are different or identical.

Examples of the B-containing group include

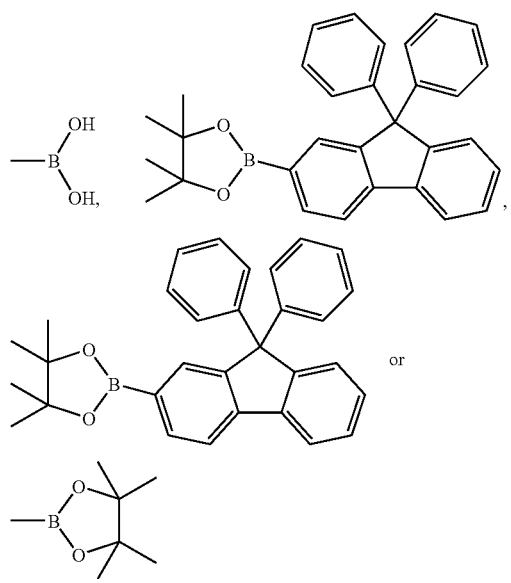

and the like, but the B-containing group is not limited thereto.

Reaction Scheme 1 below illustrates a detailed mechanism for synthesizing the dimethylenecyclohexane compound represented by Formula 1 according to an embodiment of the present invention.

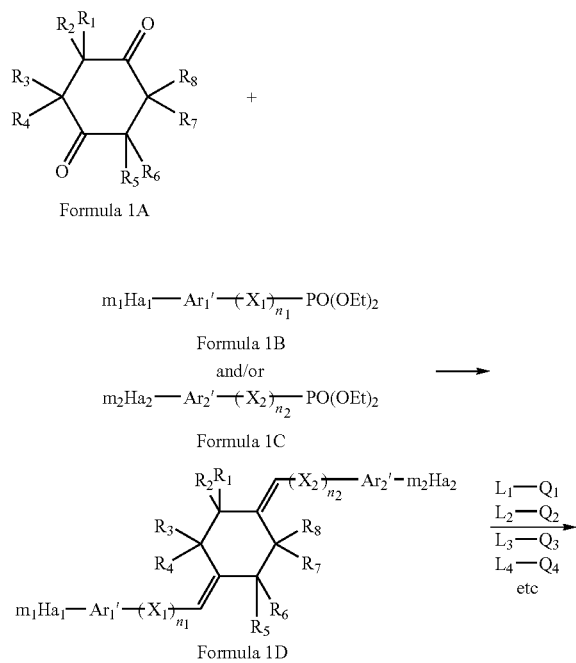

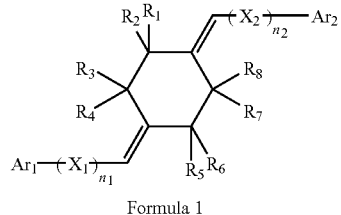

Formula 1

First, the compound represented by Formula 1A is reacted with the compounds represented by Formulae 1B and 1C to obtain the compound represented by Formula 1D. The compound represented by Formula 1A can be a commercially available compound and the compounds represented by Formulae 1B and 1C can be obtained by reacting triethyl phosphite $(P(OEt)_3)$ with an aryl compound substituted with methyl halide (for example, by reacting triethyl phosphite with bromobenzylbromide). However, methods of preparing the compounds are not limited thereto. Subsequently, the compound represented by Formula 1D is reacted with compounds represented by Formulae $L_1$-$Q_1$, $L_2$-$Q_2$, $L_3$-$Q_3$ and $L_4$-$Q_4$ to obtain the dimethylenecyclohexane compound represented by Formula 1. This reaction can be performed, for example, in the presence of $K_2CO_3$ and $Pd(PPh_3)_4$. Compounds represented by Formulae $L_1$-$Q_1$, $L_2$-$Q_2$, $L_3$-$Q_3$ and $L_4$-$Q_4$ can be boronic acids or dioxaborolanes having $L_1$, $L_2$, $L_3$ or $L_4$ or amines having $L_1$, $L_2$, $L_3$ or $L_4$, but are not limited thereto. The structures of all of the resulting compounds can be identified using 1H NMR and Mass Spectrometer.

In the method of preparing the dimethylenecyclohexane compound represented by Formula 1, $Ar_1$ and $Ar_2$ can be identical, $n_1$ and $n_2$ can be identical, $Ha_1$ and $Ha_2$ can be identical and $L_1$ and $L_2$ can be identical.

The dimethylenecyclohexane compound according to the above-described embodiment can be used in an organic light emitting device. An organic light emitting device according to an embodiment of the present invention includes a first electrode, a second electrode, and at least one organic layer disposed between the first electrode and the second electrode. The organic layer can comprise the dimethylenecyclohexane compound represented by Formula 1 as described above. In particular, the organic layer can be a hole injection layer, a hole transport layer, or an emissive layer.

The organic layer may have various structures. In other words, at least one of a hole injection layer, a hole transport layer, a hole blocking layer, an electron blocking layer, an electron transport layer, and an electron injection layer can be formed between the first electrode and the second electrode.

In particular, organic light emitting devices according to embodiments of the present invention are schematically illustrated in FIGS. 1A, 1B, and 1C. In FIG. 1A, the organic light emitting device has a first electrode 101/hole injection layer 103/emissive layer 105/electron transport layer 107/electron injection layer 109/second electrode 111 structure. In FIG. 1B, the organic light emitting device has a first electrode 101/hole injection layer 103/hole transport layer 104/emissive layer 105/electron transport layer 107/electron injection layer 109/second electrode 111 structure. In FIG. 1C, the organic light emitting device has a first electrode 101/hole injection layer 103/hole transport layer 104/emissive layer 105/hole blocking layer 106/electron transport layer 107/electron injection layer 109/second electrode 111 structure. Here, at least one of the hole injection layer 103, the hole transport layer 104 and the emissive layer 105 may include the dimethylenecyclohexane compound represented by Formula 1.

The emissive layer of an organic light emitting device according to an embodiment of the present invention may include a red, green, blue or white phosphorescent or fluorescent dopant. The phosphorescent dopant can be an organic metal compound which contains at least one of Ir, Pt, Os, Ti, Zr, Hf, Eu, Tb, and Tm.

Hereinafter, a method of manufacturing an organic light emitting device according to an embodiment of the present invention will be described with reference to the organic light emitting device illustrated in FIG. 1C.

First, a first electrode is formed by depositing or sputtering a high work-function material on a substrate. The first electrode can be an anode. The substrate, which can be any substrate that is used in conventional organic light emitting devices, may be a glass substrate or a transparent plastic substrate that has excellent mechanical strength, thermal stability, transparency, and surface smoothness, can be easily treated, and is waterproof. The first electrode can be formed of ITO, IZO, $SnO_2$, ZnO, or any transparent material which has high conductivity.

Then, a hole injection layer (HIL) can be formed on the first electrode by vacuum deposition, spin coating, casting, Langmuir Blodgett (LB) deposition, or the like.

When the HIL is formed by vacuum deposition, vacuum deposition conditions may vary according to the compound that is used to form the HIL, and the desired structure and thermal properties of the HIL to be formed. In general, however, the vacuum deposition may be performed at a deposition temperature of 100° C.-500° C., under a pressure of $10^{-8}$-$10^{-3}$ torr, at a deposition speed of 0.01-100 Å/sec, and to a layer thickness of 10 Å-5 μm.

When the HIL is formed by spin coating, coating conditions may vary according to the compound that is used to form the HIL, and the desired structure and thermal properties of the HIL to be formed. In general, however, the coating speed may be in the range of about 2,000 to 5,000 rpm, and a temperature for heat treatment, which is performed to remove a solvent after coating, may be in the range of about 80 to 200° C.

The HIL can be formed of the dimethylenecyclohexane compound represented by Formula 1 described above. Alternatively, the material may be a phthalocyanine compound, such as copperphthalocyanine disclosed in U.S. Pat. No. 4,356,429; a star-burst type amine derivative, such as TCTA, m-MTDATA, and m-MTDAPB, disclosed in Advanced Material, 6, p. 677 (1994); soluble and conductive polymer such as polyaniline/Dodecylbenzenesulfonic acid (Pani/DBSA); poly(3,4-ethylenedioxythiophene)/poly(4-styrenesulfonate (PEDOT/PSS): polyaniline/camphor sulfonic acid (Pani/CSA); (polyaniline)/poly(4-styrenesulfonate) (PANI/PSS); or the like.

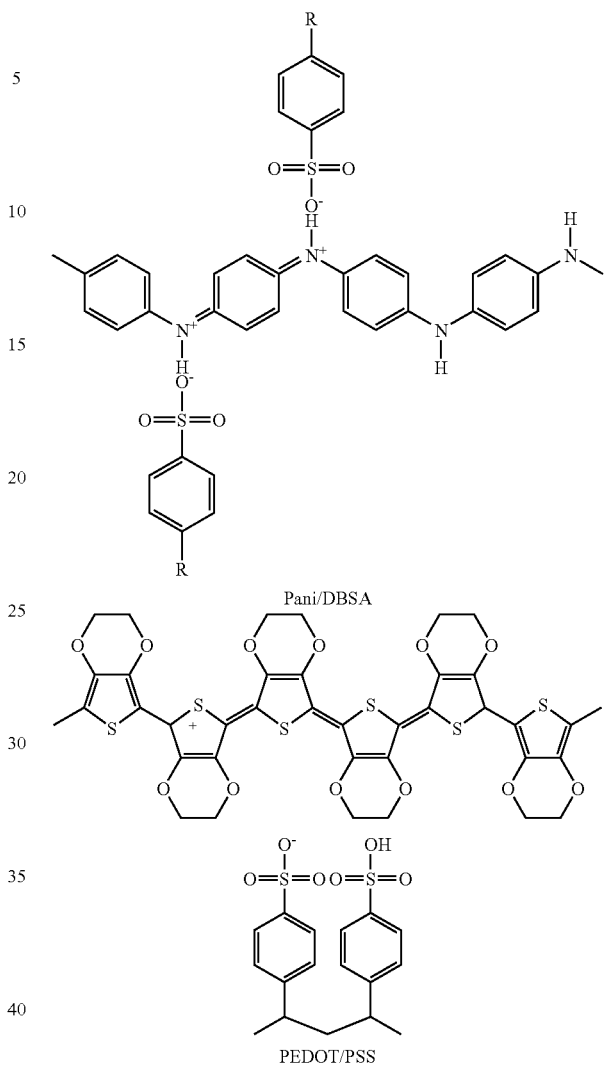

Pani/DBSA

PEDOT/PSS

The thickness of the HIL may be in the range of about 100-10,000 Å, and preferably, in the range of 100-1,000 Å. When the thickness of the HIL is less than 100 Å, the hole injecting ability of the HIL may be reduced. On the other hand, when the thickness of the HIL is greater than 10,000 Å, the driving voltage of the organic light emitting device can be increased.

Then, a hole transport layer (HTL) can be formed on the HIL using a vacuum deposition method, a spin coating method, a casting method, LB deposition, or the like. When the HTL is formed by vacuum deposition or spin coating, the conditions for deposition and coating are similar to those for the formation of the HIL, although conditions for the deposition and coating may vary according to the material that is used to form the HTL.

The HTL can be formed of the dimethylenecyclohexane compound 9 represented by Formula 1 described above. The HTL may be formed of any material that is conventionally used to form an HTL. For example, the HTL can be formed of a carbazole derivative, such as N-phenylcarbazole, polyvinylcarbazole; a typical amine derivative having an aromatic condensation ring such as N,N'-bis(3-methylphenyl)-N,N'-diphenyl-[1,1-biphenyl]-4,4'-diamine(TPD), N,N'-di(naphthalene-1-yl)-N,N'-diphenyl benzidine (α-NPD); or the like.

The thickness of the HTL may be in the range of about 50-1,000 Å, and preferably, 100-600 Å. When the thickness of the HTL is less than 50 Å, the hole transporting ability of the HTL may be reduced. On the other hand, when the thickness of the HTL is greater than 1,000 Å, the driving voltage of the organic light emitting device may increase.

Then, an emissive layer (EML) can be formed on the HTL by vacuum deposition, spin coating, casting, LB deposition, or the like. When the EML is formed by vacuum deposition or spin coating, the conditions for deposition and coating are similar to those for the formation of the HIL, although the conditions for deposition and coating may vary according to the material that is used to form the EML.

The EML may be formed of the dimethylenecyclohexane compound represented by Formula 1 according to an embodiment of the present invention. In this case, a proper host material or dopant that is known in the art can be used together with the dimethylenecyclohexane compound represented by Formula 1, or the dimethylenecyclohexane compound represented by Formula 1 can be used by itself. The host material may be, for example, $Alq_3$, 4,4'-N,N'-dicarbazole-biphenyl (CBP), or poly(n-vinylcarbazole) (PVK). As for the dopant material, examples of a fluorescent dopant include IDE102 and IDE105 obtained from Idemitsu Co., C545T obtained from Hayashibara Co., and the like, and examples of a phosphorescent dopant include a red phosphorescent dopant PtOEP, RD 61 obtained from UDC Co., a green phosphorescent dopant $Ir(PPY)_3$ (PPy=2-phenylpyridine), a blue phosphorescent dopant F2Irpic, and the like. The structure of DPAVBi represented by Formula 9 used as a dopant is shown below:

for deposition and coating may vary according to the material that is used to form the HBL. The HBL may be formed of, for example, an oxadiazole derivative, a triazole derivative, a phenanthroline derivative, or a hole blocking material disclosed in JP No. 11-329734(A1) which is incorporated herein by reference, or 2,9-dimethyl-4,7-diphenyl-1,10-phenanthroline (BCP).

The thickness of the HBL may be in the range of about 50-1,000 Å, and preferably, in the range of 100-300 Å. When the thickness of the HBL is less than 50 Å, the hole blocking ability of the HBL may be reduced. On the other hand, when the thickness of the HBL is greater than 1,000 Å, the driving voltage of the organic light emitting device may increase.

Then, an electron transport layer (ETL) is formed by vacuum deposition, spin coating, casting, or the like. When the ETL is formed by vacuum deposition or spin coating, the conditions for deposition and coating are, in general, similar to those for the formation of the HIL, although the conditions for the deposition and coating conditions may vary according to the material that is used to form the ETL. The ETL may be formed of a quinoline derivative which stably transports injected electrons from a cathode, in particular, tris(8-quinolinorate)aluminum ($Alq_3$), 3-phenyl-4-(1'-naphthyl)-5-phenyl-1,2,4-triazole (TAZ), aluminum(III)bis(2-methyl-8-quinolinato)4-phenylphenolate (Balq) or the like, which is known in the art.

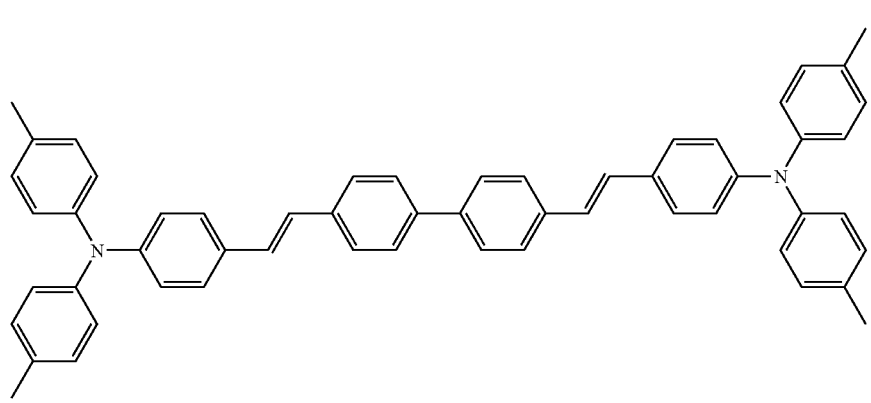

Formula 9

The concentration of the dopant is not limited, but is conventionally in the range of 0.01 to 15 parts by weight based on 100 parts by weight of the host.

The thickness of the EML may be in the range of about 100-1,000 Å, and preferably, in the range of 200-600 Å. When the thickness of the EML is less than 100 Å, the emissive ability of the EML may be reduced. On the other hand, when the thickness of the EML is greater than 1,000 Å, the driving voltage of the organic light emitting device may increase.

A hole blocking layer (HBL) can be formed on the HTL using a vacuum deposition method, a spin coating method, a casting method, LB deposition, or the like, to prevent diffusion of triplet excitons or holes into an electron transport layer when the phosphorescent dopant is used to form the EML. When the HBL is formed by vacuum deposition or spin coating, the conditions for deposition and coating are similar to those for the formation of the HIL, although the conditions

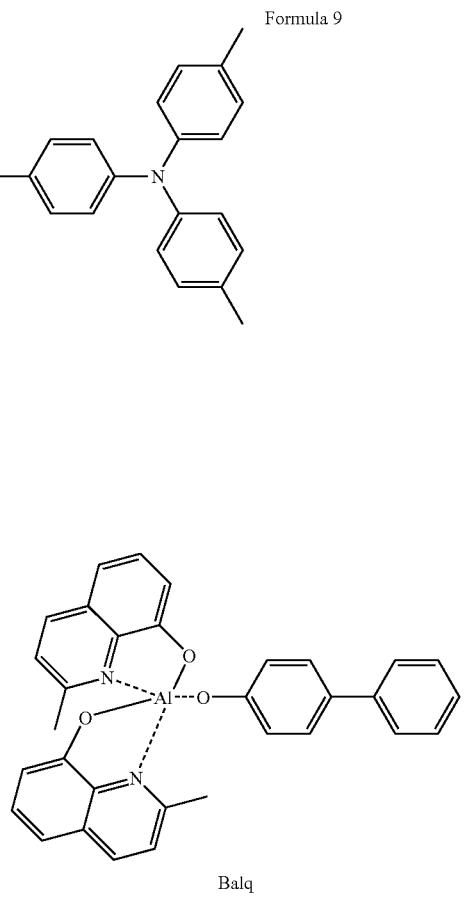

Balq

The thickness of the ETL may be in the range of about 100-1,000 Å, and preferably, 200 to 500 Å. When the thickness of the ETL is less than 100 Å, the electron transporting ability of the ETL may be reduced. On the other hand, when the thickness of the ETL is greater than 1,000 Å, the driving voltage of the organic light emitting device may increase.

Then, an electron injection layer (EIL), which is formed of a material allowing easy injection of electrons from a cathode, can be formed on the ETL. The material that is used to form the EIL is not limited.

The EIL may be formed of LiF, NaCl, CsF, $Li_2O$, BaO, or the like, which is known in the art. Conditions for the formation of the EIL are, in general, similar to conditions for the formation of the HIL, although they may vary according to the material that is used to form the EIL.

The thickness of the EIL may be in the range of about 1-100 Å, and preferably, 5-50 Å. When the thickness of the EIL is less than 1 Å, the electron injecting ability of the EIL may be reduced. On the other hand, when the thickness of the EIL is greater than 100 Å, the driving voltage of the organic light emitting device may increase.

Finally, a second electrode can be formed on the EIL by vacuum deposition, sputtering, or the like. The second electrode can be used as a cathode. The second electrode may be formed of a low work-function metal, an alloy, an electrically conductive compound, or a combination thereof. In particular, the second electrode may be formed of Li, Mg, Al, Al—Li, Ca, Mg—In, Mg—Ag, or the like. Alternatively, a transparent cathode formed of ITO or IZO can be used to produce a front surface light emitting device.

The organic light emitting device may have the first electrode/HIL/HTL/EML/HBL/ETL/EIL/second electrode structure as illustrated in FIG. 1C according to an embodiment of the present invention. However, the structure of the organic light emitting device according to the present invention may vary (for example, the structure of the organic light emitting device illustrated in FIG. 1A, which will be described in greater detail in Examples below.)

Hereinafter, Synthesis Examples and Examples of the compounds represented by Formulae 5, 7 and 8 of the present invention will be described in detail. However, the Examples are provided to facilitate the understanding of the present invention only, and are not intended to limit the scope of the present invention.

EXAMPLES

Synthesis Example 1

A compound represented by Formula 5 was synthesized through Reaction Scheme 2 below:

Reaction Scheme (2)

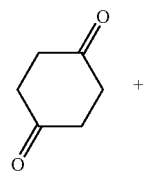

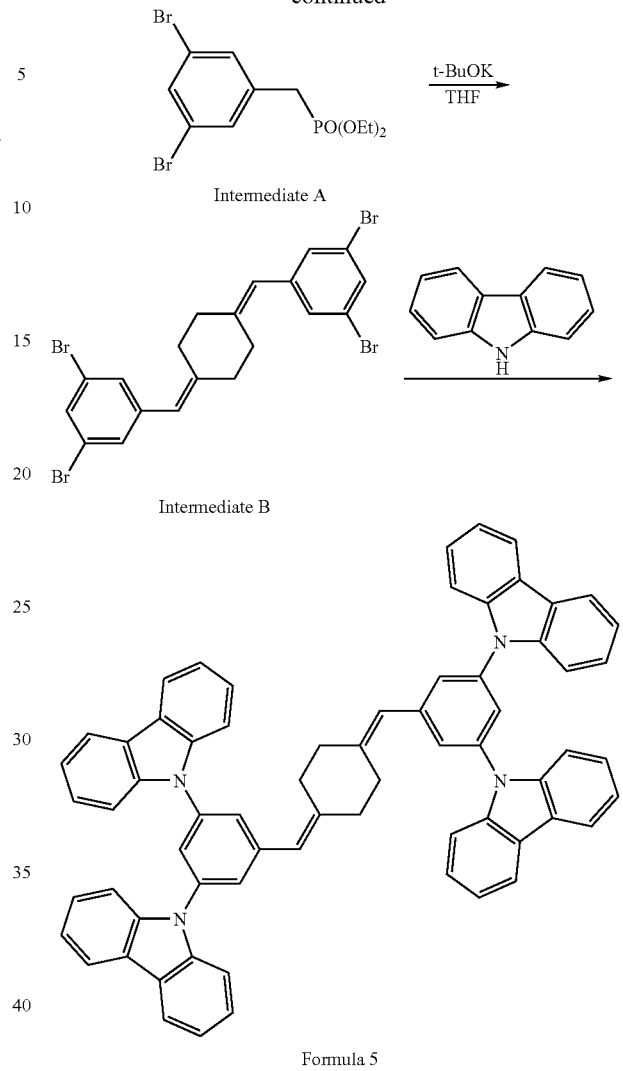

Formula 5

Synthesis of Intermediate Compound A g of 1,3-dibromotoluene (4 mmol), 1.07 g of N-bromosuccinimide (NBS) (6 mmol,) and 96 mg of benzoyl peroxide (0.4 mmol) were added to 100 ml of benzene, and the reaction mixture was refluxed for five hours. Then, the reaction mixture was purified using column chromatography and recrystallization, and vacuum-dried to obtain 881 mg of 1,3-dibromo-5-bromomethyl-benzene (yield 67%). The resultant was mixed again with 3.5 g of triethylphosphite[P(OCH$_2$CH$_3$)$_3$] (20 mmol), and stirred for twelve hours while being refluxed. The solvent was removed by decompression, and then cooled to room temperature to obtain 2.15 g of Intermediate Compound A represented by Formula 5 (yield 87%).

$^1$H-NMR (CDCl$_3$, 300 MHz, ppm): 7.41 (s, 1H), 7.16 (s, 2H), 5.22 (s, 2H), 3.11-3.32 (m, 4H), 1.21 (t, 6H).

Synthesis of Intermediate Compound B 3.86 g of Intermediate Compound A (10 mmol) and 0.5 g of cyclohexane-1,4-dione (4.5 mmol) were dissolved in 300 ml of tetrahydrofuran (THF), and then 1.25 g of t-BuOK (11 mmol) was added to the reaction mixture and reacted at 60° C. for one day. Then, the resultant was left sit, a supernatant thereof was collect, and the solvent was removed. Thereafter, 100 ml of methanol was added to the resulting product, and the resultant was filtered and then washed again with methanol. Subsequently, the resultant was separated and purified using silica gel column chromatography (CHCl$_3$) to obtain 9.7 g of Intermediate Compound B (Yield 58%).

5 g (40 mmol) of 1,4-cyclohexadion was added to the mixture and reacted at 70° C. for one day. After 20 ml of ethanol was added to the mixture and dried in a vacuum, 200 ml of methylene chloride was added to the dried mixture. An organic layer collected from the mixture was washed twice with 200 ml of water and dried over anhydrous magnesium sulfate to evaporate the solvent. The dried result was purified using silica gel column chromatography to obtain 2.2 g of Intermediate Compound B (Yield 83%).

$^1$H-NMR (CDCl$_3$, 300 MHz, ppm): 7.85 (s, 2H), 7.10 (d, 4H), 6.25 (s, 2H), 2.53-2.31 (m, 8H).

Synthesis of Compound of Formula 5

5.76 g of Intermediate Compound B (10 mmol) was dissolved in 200 ml of o-Xylene, and 10 g of carbazole (60 mmol), 3.7 g of Pd$_2$ dba$_3$ (4.0 mmol), 0.6 g of P(t-Bu)$_3$ (3.0 mmol) and 5.8 g of sodium t-butoxide (60 mmol) were added to the reaction mixture. Then, the mixture was stirred for twenty four hours at a reflux temperature. The resultant was cooled to room temperature, and then the solvent was removed and the resulting product was separated and purified using silica gel column chromatography and recrystallization to obtain 4.1 g of a white powder represented by Formula 5 (Yield 45%).

$^1$H-NMR (CDCl$_3$, 300 MHz, ppm): 8.15 (m, 8H), 7.6-7.2 (m, 30H), 6.15 (s, 2H), 2.53-2.30 (m, 8H).

Synthesis Example 2

A compound of Formula 7 was synthesized through Reaction Scheme 3 below:

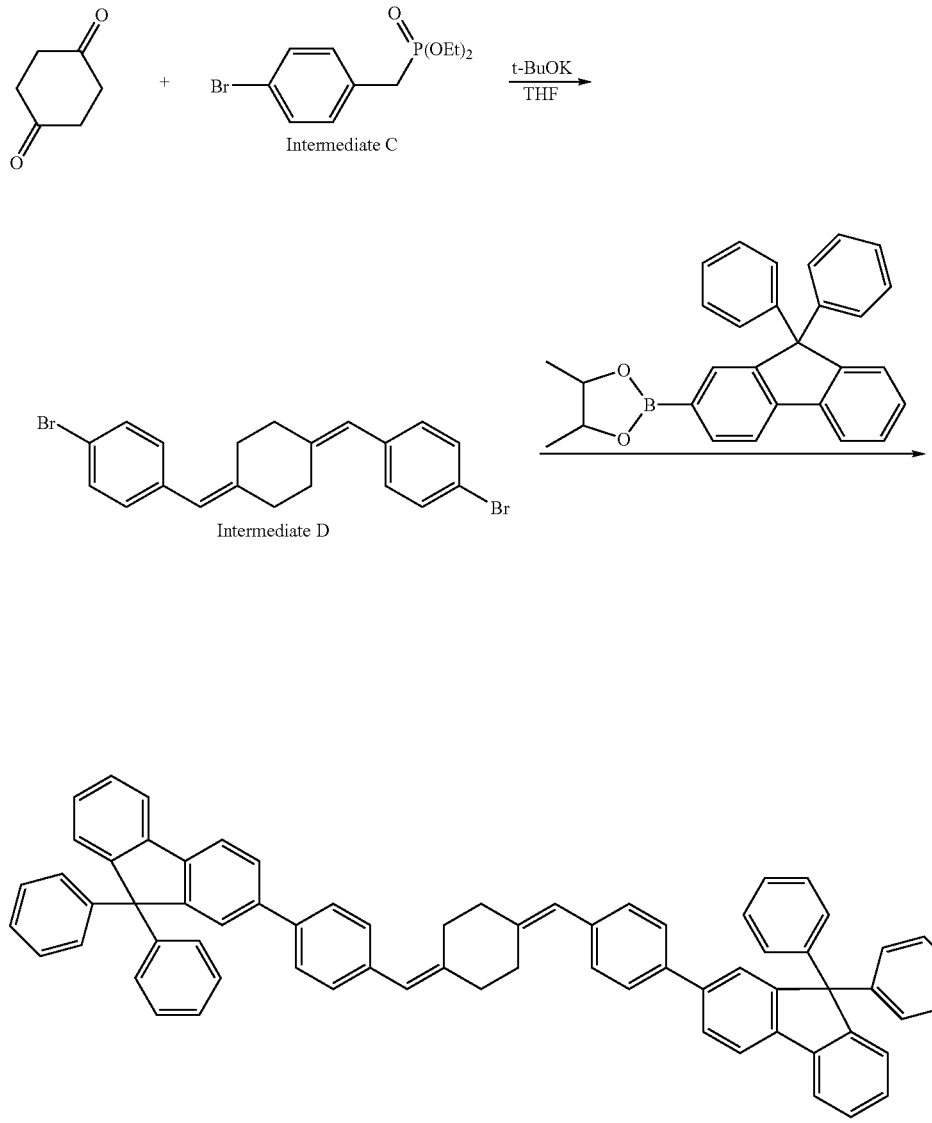

Formula 7

Synthesis of Intermediate Compound C 10 g of 4-bromobenzyl bromide (40 mmol) was mixed with 13.3 g of triethylphosphite ($P(OCH_2CH_3)_3$) (80 mmol), and the mixture was stirred at 185° C. for 6 hours. The solvent was removed by drying the mixture under pressure, and then the resultant was cooled to room temperature to obtain 11.8 g of white solid powder (yield: 96%).

$^1$H-NMR (CDCl$_3$, 300 MHz, ppm): 7.42 (d, 2H), 7.18 (d, 2H), 4.02 (m, 4H), 3.12 (s, 1H), 3.05 (s, 1H), 1.25 (t, 6H)

Synthesis of Intermediate Compound D 31.6 g of Intermediate Compound C (100 mmol) was dissolved in 300 ml of tetrahydrofuran (THF), and then 12.5 g of t-BuOK (110 mmol) was added to the mixture and the resultant was reacted at 20° C. for 1 hour. Then, 5 g of 1,4-cyclohexanedione (40 mmol) was added to the resultant and the resulting mixture was reacted at 70° C. for one day, and 20 ml of ethanol was added to the mixture and the mixture was dried under a vacuum. Thereafter, 200 ml of methylene chloride was added to the resultant. An organic layer collected from the resultant was washed twice with 200 ml of water, dried by adding anhydrous magnesium sulfate, and then filtered to dry a compound of Formula 11 (14.9 mmol), 0.5 g of tri(dibenzylideneacetone)dipalladium(0) (Pd$_2$(dba)$_3$) (0.54 mmol), 0.083 g of t-butylphosphine (0.41 mmol) and 2.88 g of NaO-t-Bu (30 mmol) were added to the mixture and the mixture was stirred at room temperature for 4 hours. After the reaction was terminated, 100 ml of dichloromethane was added to the resultant and the mixture was washed twice using 100 ml of water. Then, an organic layer was collected and dried with anhydrous magnesium sulfate, and then the solvent was vaporized to obtain a product. Thereafter, the product was separated and purified using silica gel column chromatography and recrystallized to obtain 3.7 g of a compound of Formula 7 (Yield 55%).

$^1$H-NMR (CDCl$_3$, 300 MHz, ppm): 7.81 (m, 4H), 7.64 (m, 4H), 7.54-7.52 (m, 6H), 7.41 (m, 6H), 7.3-7.2 (m, 22H), 6.34 (s, 2H), 2.61-2.37 (m, 8H)

Synthesis Example 3

A compound of Formula 8 was synthesized through Reaction Scheme 4 below:

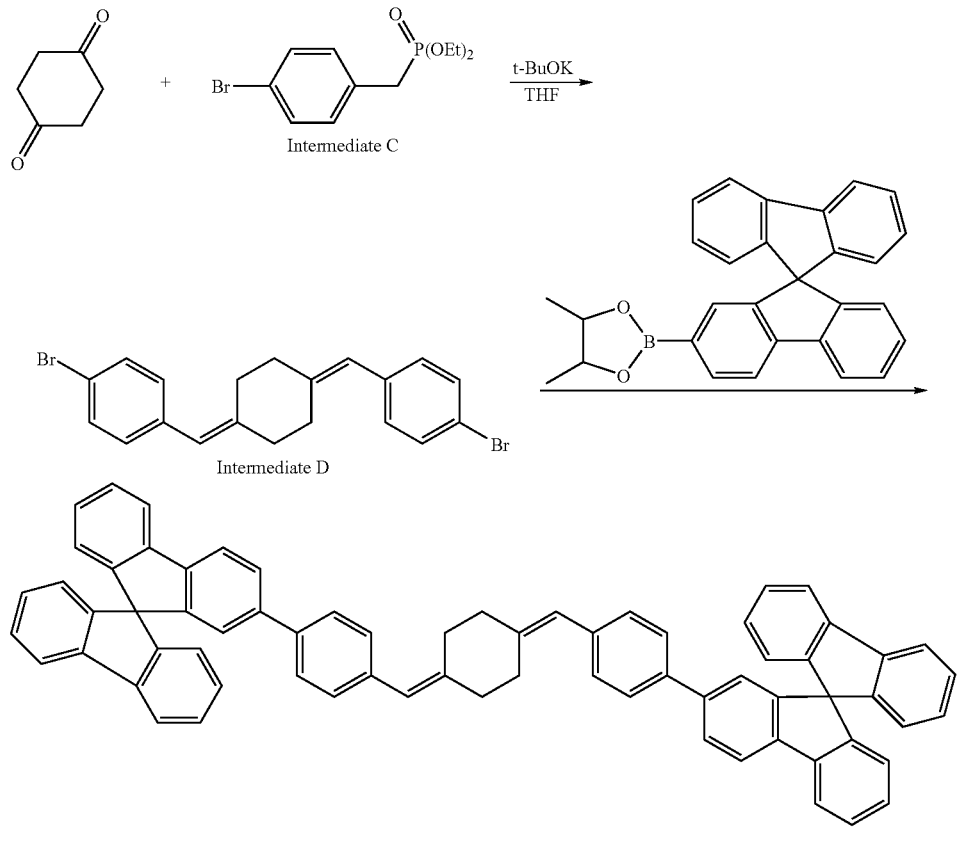

Reaction Scheme 4

Formula 8 only the solvent. Subsequently, the resultant product was separated and purified using silica gel column chromatography to obtain 9.7 g of Intermediate Compound D (Yield 58%).

$^1$H-NMR (CDCl$_3$, 300 MHz, ppm): 7.42 (d, 4H), 7.10 (d, 4H), 6.25 (s, 2H), 2.53-2.31 (m, 8H)

4.45 g of the obtained Intermediate Compound D (10.6 mmol) was dissolved in 80 ml of o-xylene, and then 6.62 g of The Intermediate Compound C and Intermediate Compound D were prepared in the same manner as in Synthesis Example 2. 4.45 g of the obtained Intermediate Compound D (10.6 mmol) was dissolved in 80 ml of o-xylene, and then 6.59 g of a compound of Formula 12 (14.9 mmol), 0.5 g of tri(dibenzylideneacetone)dipalladium(0) (Pd$_2$(dba)$_3$) (0.54 mmol), 0.083 g of t-butylphosphine (0.41 mmol) and 2.88 g of NaO-t-Bu (30 mmol) were added to the mixture and the mixture was stirred at room temperature for 4 hours. After the reaction was terminated, 100 ml of dichloromethane was added to the resultant and the mixture was washed twice using 100 ml of water. Then, an organic layer was obtained and dried with anhydrous magnesium sulfate, and then the solvent was vaporized to obtain a product. Thereafter, the product was separated and purified using silica gel column chromatography and recrystallized to obtain 2.9 g of a compound of Formula 8 (Yield 44%).

$^1$H-NMR (CDCl$_3$, 300 MHz, ppm): 8.13 (m, 4H), 7.84 (m, 4H), 7.60-7.50 (m, 4H), 7.39 (m, 6H), 7.3-7.2 (m, 22H), 6.32 (s, 2H), 2.59-2.39 (m, 8H)

Example 1

Using the compound of Formula 7 as a host of an emissive layer, an organic light emitting device having the following structure was manufactured:

ITO/α-NPD(750 Å)/5 weight % Ir(piq)3 (Compound 7) (350 Å)/Balq(50 Å/Alq$_3$(180 Å)/LiF(10 Å)/Al(2000 Å)

As an anode, a 15 Ω/cm$^2$ (1000 Å) ITO glass substrate was cut to a size of 50 mm×500 mm×0.7 mm, ultrasonic washed with acetone, isopropyl alcohol and pure water for 15 minutes each respectively, and then washed with UV ozone for 15 minutes. The resulting substrate was referred to as Substrate 1. α-NPD was vacuum deposited on Substrate 1 to form a hole transport layer with a thickness of 750 Å. The host and guest compound, Ir(piq)$_3$, was vacuum deposited on the hole transport layer to form an emissive layer with a thickness of 350 Å. Then, Alq$_3$ was vacuum deposited on the emissive layer to form an electron transport layer with a thickness of 180 Å. LiF and Al were sequentially vacuum deposited on the electron transport layer to form an electron injection layer with a thickness of 10 Å and a cathode with a thickness of 2,000 Å, respectively. As a result, an organic light emitting device as illustrated in FIG. 1A was manufactured.

Example 2

Using the compound of Formula 7 as a host of an emissive layer, an organic light emitting device having the following structure was manufactured:

ITO/PEDOT (500 Å)/5 weight % Ir(piq)3 (Compound 7) (550 Å)/Balq (50 Å)/Alq3 (180 Å)/LiF (10 Å)/Al (2000 Å)

As an anode, a 15 Ω/cm$^2$ (1000 Å) ITO glass substrate was cut to a size of 50 mm×500 mm×0.7 mm, ultrasonic washed with acetone, isopropyl alcohol and pure water for 15 minutes each respectively, and then washed with UV ozone for 15 minutes. The resulting substrate was referred to as Substrate 1. PEDOT was deposited on Substrate 1, and then the resultant was heat-treated under the ambient environment conditions at 110° C. for 5 minutes, and heat-treated again under a nitrogen atmosphere at 200° C. for 10 minutes to form a hole transport layer with a thickness of 500 Å. A mixed solution of a host compound and a guest compound (1. Compound 7 (neat), 2. CH24+red dopant (5 weight %), 3. CH25+red dopant (5 weight %)=1 wt % in dichloromethane) was spin coated on the hole transport layer, and then the resultant was heat-treated at 110° C. for 30 minutes to form an emissive layer with a thickness of 550 Å. Then, Balq and Alq$_3$ were vacuum deposited on the emissive layer to thicknesses of 50 Å and 180 Å, respectively, to form an electron transport layer. LiF and Al were sequentially vacuum deposited on the electron transport layer to form an electron injection layer with a thickness of 10 Å and a cathode with a thickness of 2,000 Å, respectively. As a result, an organic light emitting device as illustrated in FIG. 1A was manufactured.

Example 3

An organic light emitting device was manufactured in the same manner as in Example 1, except that a compound of Formula 8 was used as a host compound of an emissive layer instead of the compound of Formula 7 used in Example 1.

Example 4

An organic light emitting device was manufactured in the same manner as in Example 2, except that a compound of Formula 8 was used as a host compound of an emissive layer instead of the compound of Formula 7 used in Example 2.

Experimental Example

With respect to the organic light emitting devices manufactured using the compound of Formula 7 and the compound of Formula 8, and the organic light emitting devices manufactured in Examples 1 through 4, the driving voltage, color purity, emission efficiency, best luminance, current density and EL peak wavelength of each of the organic light emitting devices were measured using a PR650 (Spectroscan) source measurement unit. The results are shown in Tables 1 and 2 below.

TABLE 1

|  | Turn on Voltage [V] | CIE color coordinate [100 cd basis] | | Driving voltage [V] and efficiency [cd/A] | | | | | |
| --- | --- | --- | --- | --- | --- | --- | --- | --- | --- |
|  |  | x | y | 100 cd | | 600 cd | | 1200 cd | |
| Compound 7 | 6 | 0.2565 | 0.4369 | 11.2 V | 0.056 | — | — | — | — |
| Compound 8 | 12.6 | — | — | — | — | — | — | — | — |
| Example 1 | 4.2 | 0.6654 | 0.3198 | 6 V | 5.64 | 7.6 V | 6.73 | 8.4 V | 8 |
| Example 2 | 9.2 | 0.6713 | 0.3264 | 16 V | 0.426 | 18.8 V | 0.65 | 20 V | 0.5 |
| Example 3 | 3.8 | 0.6705 | 0.3216 | 5.2 V | 6.45 | 6.8 V | 7.64 | 7.8 V | 9.44 |
| Example 4 | 5.6 | 0.6739 | 0.3242 | 14.6 V | 0.59 | 18 V | 0.71 | 19.6 V | 0.51 |

TABLE 2

|  | Best luminance | Current density (@100 cd) | EL spectrum (@100 cd) |
| --- | --- | --- | --- |
| Compound 7 | 158 | 5.94 (mA/cm2) | — |
| Compound 8 | 92 | 164.5 (mA/cm2) | — |

TABLE 2-continued

| | Best luminance | Current density (@100 cd) | EL spectrum (@100 cd) |
|---|---|---|---|
| Example 1 | >7231 | 1.77 (mA/cm2) | 630 nm |
| Example 2 | 1929 | 23.4 (mA/cm2) | 628 nm |
| Example 3 | >7466 | 1.55 (mA/cm2) | 630 nm |

From the results in Tables 1 and 2, it can be confirmed that since Compound 7, Compound 8 and the organic light emitting devices manufactured using the same used a red light emitting material for deposition, they exhibited better results in a deposition process compared with a spin process, but Compound 7 and Compound 8 can be a host material of a red light emitting material both in a spin process and deposition process.

The dimethylenecyclohexane compound represented by Formula 1 according to the present invention has excellent luminous characteristics and thermal stability. Accordingly, an organic light emitting device using the dimethylenecyclohexane compound according to the present invention exhibits a low driving voltage, excellent color purity and high efficiency.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A dimethylenecyclohexane compound represented by Formula 1:

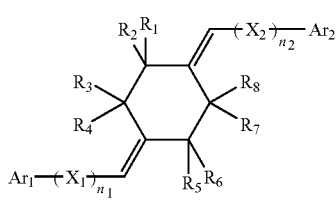

(1)

where $R_1$, $R_2$, $R_3$, $R_4$, $R_5$, $R_6$, $R_7$ and $R_8$ are each independently a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group represented by —N(Z')(Z") where Z' and Z" are each independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group;

each of $X_1$ and $X_2$ is independently a single bond, a double bond, a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_1$-$C_{20}$ heteroalkylene group, a substituted or unsubstituted $C_7$-$C_{30}$ alkylenearylene group, a substituted or unsubstituted $C_6$-$C_{30}$ arylene group, or a substituted or unsubstituted $C_2$-$C_{30}$ heteroarylene group;

$n_1$ and $n_2$ are each independently an integer in the range of 0 to 5, and when $n_1$ or $n_2$ is 2 or greater, the $X_1$s or $X_2$s can be respectively identical or different;

$Ar_1$ and $Ar_2$ are each independently a substituted or unsubstituted $C_6$-$C_{30}$ aryl group, a substituted or unsubstituted $C_2$-$C_{30}$ heteroaryl group, a substituted or unsubstituted $C_4$-$C_{30}$ cycloalkyl group or a substituted or unsubstituted $C_2$-$C_{30}$ cycloheteroalkyl group; and at least one of $Ar_1$ and $Ar_2$ includes at least two substituents, the substituents included in $Ar_1$ or $Ar_2$ are each independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or a substituted amino group represented by —N(R')(R"), where R' and R" are each independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a $C_5$-$C_{20}$ cycloalkyl group, or a $C_5$-$C_{30}$ heterocycloalkyl group.

2. The dimethylenecyclohexane compound of claim 1, wherein $X_1$ and $X_2$ are each independently one selected from the group consisting of a single bond, a methylene group, an ethylene group, a —O— methylene group, a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluoromethoxyphenylene group, an o-, m-, or p-tolylene group, an o-, m- or p-cumenylene group, a mesitylene group, a phenoxyphenylene group, a (α,α-dimethylbenzene)phenylene group, a (N,N'-dimethyl)aminophenylene group, a (N,N'-diphenyl)aminophenylene group, a ($C_1$-$C_{10}$ alkylcyclohexyl)phenylene group, a (anthracenyl)phenylene group, a pentalenylene group, an indenylene group, a naphthylene group, a $C_1$-$C_{10}$ alkylnaphthylene group, a $C_1$-$C_{10}$ alkoxynaphthylene group, a halonaphthylene group, a cyanonaphthylene group, a biphenylenylene group, a $C_1$-$C_{10}$ alkyl biphenylenylene group, a $C_1$-$C_{10}$ alkoxy biphenylenylene group, an anthracenylene group, an azulenylene group, a heptalenylene group, an acenaphthylenylene group, a phenalenylene group, a fluorenylene group, a methylanthrylene group, a phenanthrenylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylenylene group, a hexaphenylene group, a hexacenylene group, a rubicenylene group, a coronenylene group, a trinaphthylenylene group, a heptaphenylene group, a heptacenylene group, a pyranthrenylene group, an ovalenylene group, a carbazolylene group, a $C_{1-10}$ alkyl carbazolylene group, a thiophenylene group, an indolylene group, a purinylene group, a benzimidazolylene group, a quinolinylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridinylene group, a pyridazinylene group, a pyrimidinylene group, a pyrazinylene group, and a thianthrenylene group.

3. The dimethylenecyclohexane compound of claim 1, wherein $n_1$ and $n_2$ are each independently an integer of 0, 1, 2 or 3.

4. The dimethylenecyclohexane compound of claim 1, wherein said at least two substituents included in $Ar_1$ or $Ar_2$ are each independently one selected from the group consisting of a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a ($C_1$-$C_{10}$ alkylcyclohexyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenylenyl group, a $C_1$-$C_{10}$ alkoxy biphenylenyl group, an anthracenyl group, $C_1$-$C_{10}$ alkyl anthracenyl group, a $C_1$-$C_{10}$ alkoxy anthracenyl group, an azulenyl group, a heptalenyl group, an acenaphthylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a $C_1$-$C_{10}$ alkyl carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, a $C_1$-$C_{10}$ alkylcyclohexyl group, a $C_1$-$C_{10}$ alkoxycyclohexyl group, an oxyranyl group, a pyrrolidinyl group, a pyrazolidinyl group, an imidazolidinyl group, a piperidinyl group, a piperazinyl group, a morpholinyl group, a carbazole group and an amino group represented by —N(R')(R") where R' and R" are each independently one selected from the group consisting of a hydrogen atom, a phenyl group, a $C_1$-$C_{10}$ alkyl phenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a ($C_1$-$C_{10}$ alkylcyclohexyl)phenyl group, an anthracenyl phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group and a $C_1$-$C_{10}$ alkyl biphenylenyl group.

5. The dimethylenecyclohexane compound of claim 1, wherein said at least two substituent included in $Ar_1$ or $Ar_2$ are each a carbazole group.

6. The dimethylenecyclohexane compound of claim 1, wherein the compound represented by Formula 1 is a compound represented by Formula 2:

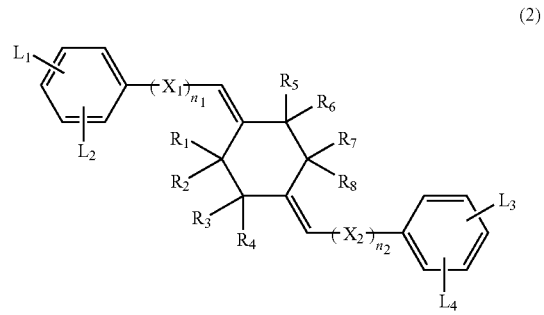

(2)

where $R_1$, $R_2$, $R_3$, $R_4$, $R_5$, $R_6$, $R_7$, $R_8$, $X_1$, $X_2$, $n_1$ and $n_2$ are the same as defined in Formula 1; and each of $L_1$, $L_2$, $L_3$ and $L_4$ is independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or an amino group represented by —N(R')(R") where each of R' and R" is independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group.

7. The dimethylenecyclohexane compound of claim 1, wherein the compound represented by Formula 1 is a compound represented by Formula 3 or 4:

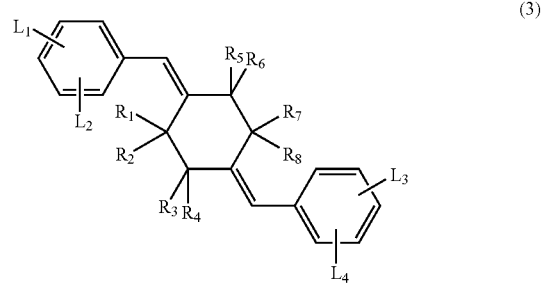

(3)

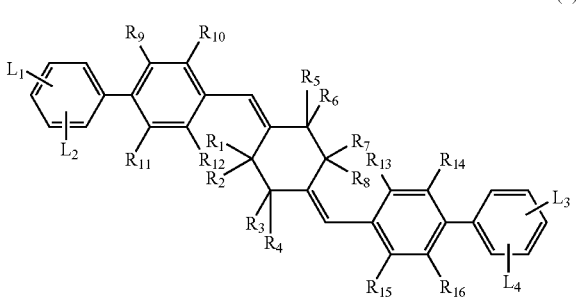

(4)

where $R_1$, $R_2$, $R_3$, $R_4$, $R_5$, $R_6$, $R_7$, $R_8$, $X_1$, $X_2$, $n_1$ and $n_2$ are the same as defined in claim 1;

each of $L_1$, $L_2$, $L_3$ and $L_4$ is independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or an amino group represented by —N(R')(R") where each of R' and R″ is independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group; and each of $R_9$, $R_{10}$, $R_{11}$, $R_{12}$, $R_{13}$, $R_{14}$, $R_{15}$ and $R_{16}$ is independently a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group represented by —N(Z′)(Z″); and each of Z′ and Z″ is independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group.

8. The dimethylenecyclohexane compound of claim 1, wherein the compound represented by Formula 1 is a compound represented by one selected from the group consisting of Formulae 5 through 8:

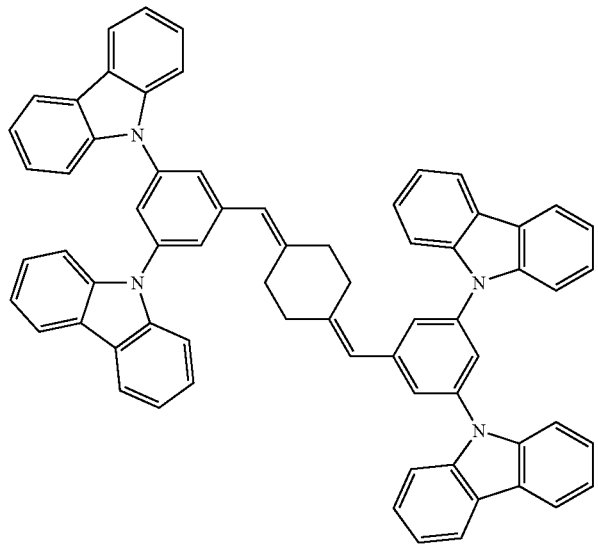

(5)

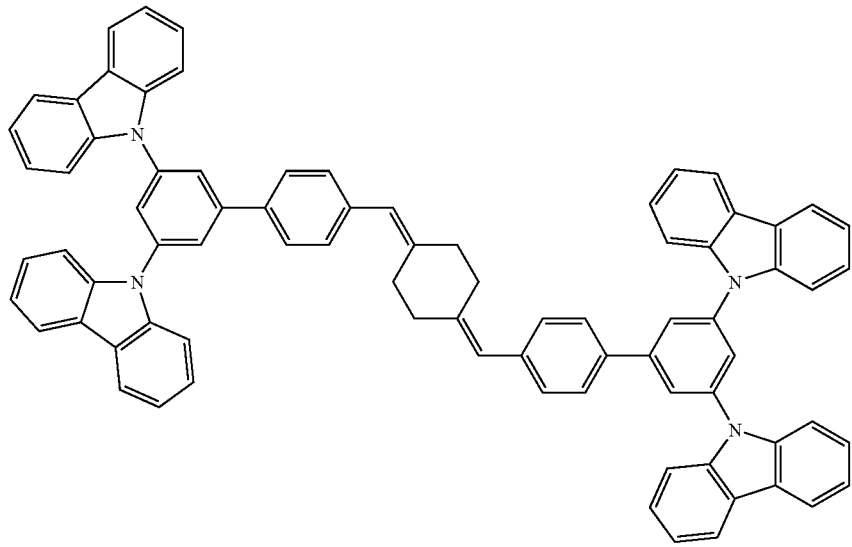

(6)

-continued (7)
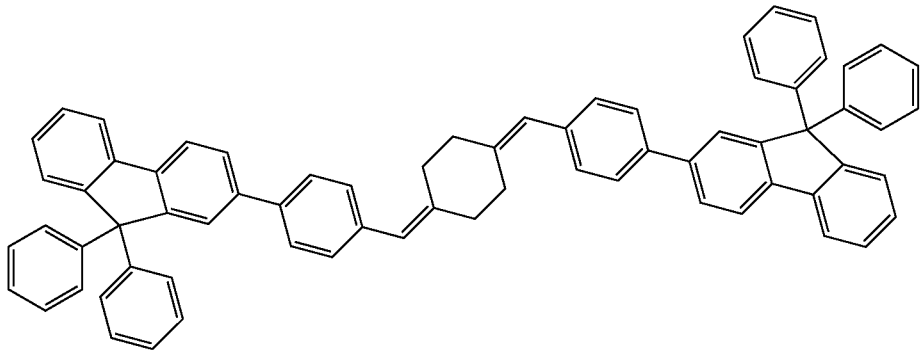

(8)
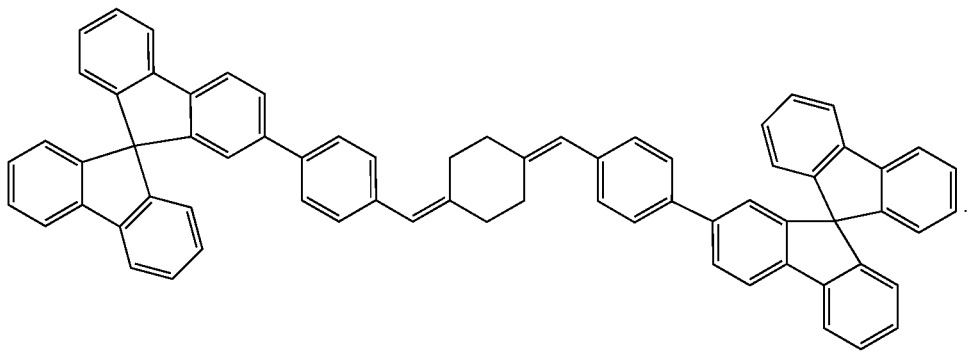

9. A method of preparing a dimethylenecyclohexane compound represented by Formula 1, the method comprising:

reacting a compound represented by Formula 1A with a compound represented by Formula 1B and a compound represented by Formula 1C to obtain a compound represented by Formula 1D; and reacting the compound represented by Formula 1D with compounds including at least one of (1) a compound represented by Formula 1E and the compound represented by 1F, and (2) a compound represented by Formula 1G and a compound represented by Formula 1H to obtain the compound represented by Formula 1:

(1A)

[Formula 1A structure: cyclohexane-1,4-dione with $R_1$–$R_8$ substituents]

$m_1Ha_1\text{-}Ar_1'\text{-}(X_1)_{\overline{n_1}}PO(OEt)_2$ (1B)

$m_2Ha_2\text{-}Ar_2'\text{-}(X_2)_{\overline{n_2}}PO(OEt)_2$ (1C)

(1D)
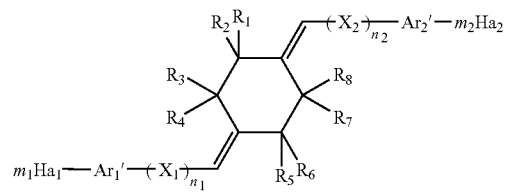

$L_1\text{-}Q_1$ (1E)

$L_2\text{-}Q_2$ (1F)

$L_3\text{-}Q_3$ (1G)

$L_4\text{-}Q_4$ (1H)

(1)

[Formula 1 structure with $Ar_1$–$(X_1)_{n_1}$ and $(X_2)_{n_2}$–$Ar_2$ substituents on cyclohexane with $R_1$–$R_8$]

where each of $R_1$, $R_2$, $R_3$, $R_4$, $R_5$, $R_6$, $R_7$ and $R_8$ is independently a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group represented by —N(Z')(Z"), and each of Z' and Z" is independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group or a substituted or unsubstituted $C_5$-$C_{30}$ heterocycloalkyl group;

each of $X_1$ and $X_2$ is independently a single bond, a double bond, a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_1$-$C_{20}$ heteroalkylene group, a substituted or unsubstituted $C_7$-$C_{30}$ alkylenearylene group, a substituted or unsubstituted $C_6$-$C_{30}$ arylene group, or a substituted or unsubstituted $C_2$-$C_{30}$ heteroarylene group;

each of $n_1$ and $n_2$ is independently an integer in the range of 0 to 5, and when $n_1$ or $n_2$ is 2 or greater, the $X_1$s or $X_2$s are each independently identical or different;

each of $Ar_1'$ and $Ar_2'$ is independently a substituted or unsubstituted $C_6$-$C_{30}$ aryl group, a substituted or unsubstituted $C_2$-$C_{30}$ heteroaryl group, a substituted or unsubstituted $C_4$-$C_{30}$ cycloalkyl group or a substituted or unsubstituted $C_2$-$C_{30}$ cycloheteroalkyl group;

each of $Ha_1$ and $Ha_2$ is a halogen atom;

each of $m_1$ and $m_2$ is an integer in the range of 0 to 5, and at least either one of $m_1$ and $m_2$ is an integer of 1 or greater;

Formula 1B and Formula 1C are the same or different from each other;

$L_1$, $L_2$, $L_3$ and $L_4$ are each independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or a substituted amino group represented by —N(R')(R") where each of R' and R" is independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group;

$Q_1$, $Q_2$, $Q_3$, $Q_4$ are each independently a B-containing group, or H when $L_1$, $L_2$, $L_3$ and $L_4$ are substituted amino groups represented by —N(R')(R");

$Ar_1$ and $Ar_2$ are each independently a substituted or unsubstituted $C_6$-$C_{30}$ aryl group, a substituted or unsubstituted $C_2$-$C_{30}$ heteroaryl group, a substituted or unsubstituted $C_4$-$C_{30}$ cycloalkyl group or a substituted or unsubstituted $C_2$-$C_{30}$ cycloheteroalkyl group; and at least one of $Ar_1$ and $Ar_2$ includes at least two substituents, the substituents included in $Ar_1$ or $Ar_2$ are each independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or a substituted amino group represented by —N(R')(R"), where R' and R" are each independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a $C_5$-$C_{20}$ cycloalkyl group, or a $C_5$-$C_{30}$ heterocycloalkyl group.

10. The method of claim 9, wherein $R_1$ through $R_8$ are each hydrogen, $Ar_1'$ and $Ar_2'$ are each a phenyl group, $X_1$ and $X_2$ are each a methylene group, $m_1$ and $m_2$ are each 2, $Ha_1$ and $Ha_2$ are each Br, and the compounds represented by Formulae 1D to 1H are each carbazole.

11. The method of claim 9, wherein $R_1$ through $R_8$ are each hydrogen, $Ar_1'$ and $Ar_2'$ are each a phenyl group, $X_1$ and $X_2$ are each a methylene group, $m_1$ and $m_2$ are each 1, $Ha_1$ and $Ha_2$ are each Br, and the compounds represented by Formulae 1D to 1H are the same and are represented by

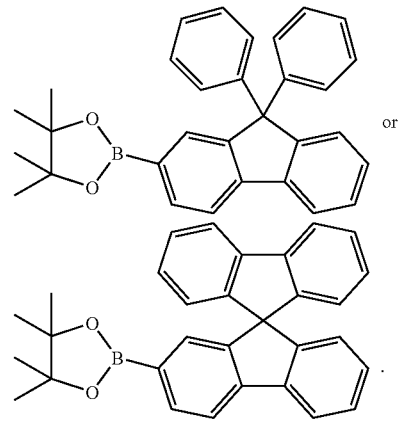

12. The dimethylenecyclohexane compound prepared by the method of claim 9.

13. An organic light emitting device, comprising:
a first electrode;
a second electrode; and
at least one organic layer interposed between the first electrode and the second electrode, said at least one organic layer comprising a layer comprised of a dimethylenecyclohexane compound represented by Formula 1:

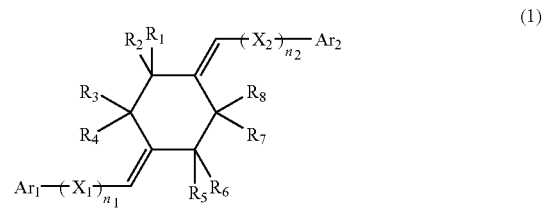

(1)

where $R_1$, $R_2$, $R_3$, $R_4$, $R_5$, $R_6$, $R_7$ and $R_8$ are each independently a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group represented by —N(Z')(Z"), Z' and Z" are each independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group;

each of $X_1$ and $X_2$ is independently a single bond, a double bond, a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_1$-$C_{20}$ heteroalkylene group, a substituted or unsubstituted $C_7$-$C_{30}$ alkylenearylene group, a substituted or unsubstituted $C_6$-$C_{30}$ arylene group, or a substituted or unsubstituted $C_2$-$C_{30}$ heteroarylene group;

$n_1$ and $n_2$ are each independently an integer in the range of 0 to 5, and when $n_1$ or $n_2$ is 2 or greater, the $X_1$s or $X_2$s can be respectively identical or different;

$Ar_1$ and $Ar_2$ are each independently a substituted or unsubstituted $C_6$-$C_{30}$ aryl group, a substituted or unsubstituted $C_2$-$C_{30}$ heteroaryl group, a substituted or unsubstituted $C_4$-$C_{30}$ cycloalkyl group or a substituted or unsubstituted $C_2$-$C_{30}$ cycloheteroalkyl group; and at least one of $Ar_1$ and $Ar_2$ includes at least two substituents, the substituents included in $Ar_1$ or $Ar_2$ are each independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or a substituted amino group represented by —N(R')(R") where R' and R" are each independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a $C_5$-$C_{20}$ cycloalkyl group, or a $C_5$-$C_{30}$ heterocycloalkyl group.

14. The organic light emitting device of claim 13, wherein the layer comprised of the dimethylenecyclohexane compound is a hole injection layer.

15. The organic light emitting device of claim 13, wherein the layer comprised of the dimethylenecyclohexane compound is a hole transport layer.

16. The organic light emitting device of claim 13, wherein the layer comprised of the dimethylenecyclohexane compound is an emissive layer.

17. The organic light emitting device of claim 13, wherein the organic layer further comprises at least one layer selected from the group consisting of a hole injection layer, a hole transport layer, an electron blocking layer, a hole blocking layer, an electron transport layer and an electron injection layer.

18. The organic light emitting device of claim 13, wherein said at least one organic layer comprises a hole injection layer formed on the first electrode, an emissive layer formed on the hole injection layer, an electron transport layer formed on the emissive layer, and an electron injection layer formed on the electron transport layer, optionally a hole transport layer formed between the hole injection layer and the emissive layer, and optionally a hole blocking layer formed between the emissive layer and the electron transport layer.

19. The organic light emitting device of claim 18, wherein at least one of the hole injection layer, the hole transport layer and the emissive layer include the dimethylenecyclohexane compound represented by Formula 1.

20. The organic light emitting device of claim 13, wherein the dimethylenecyclohexane compound represented by Formula 1 is a compound represented by one of Formulae 2 to 4:

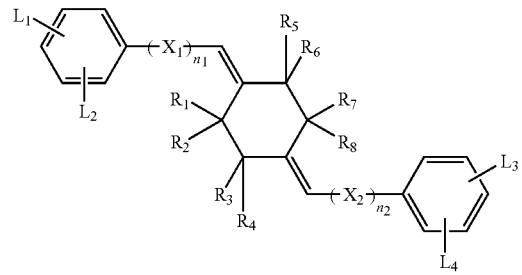

(2)

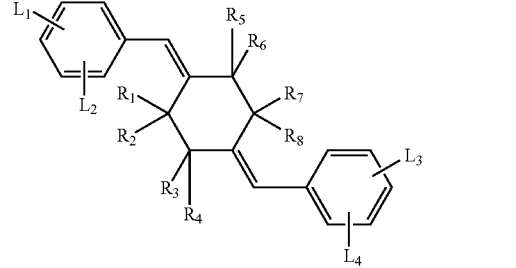

(3)

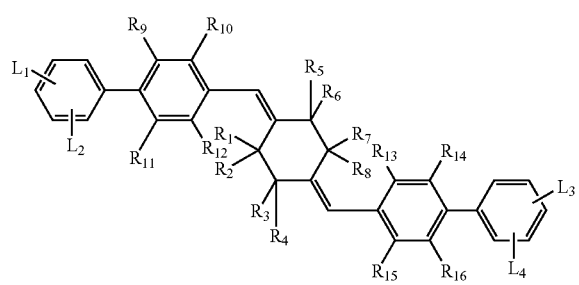

(4)

where $R_1$, $R_2$, $R_3$, $R_4$, $R_5$, $R_6$, $R_7$, $R_8$, $X_1$, $X_2$, $n_1$ and $n_2$ are the same as defined in Formula 1; and each of $L_1$, $L_2$, $L_3$ and $L_4$ is independently a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, a substituted or unsubstituted $C_5$-$C_{30}$ heterocycloalkyl group, or an amino group represented by —N(R')(R") where each of R' and R" is independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group; and each of $R_9$, $R_{10}$, $R_{11}$, $R_{12}$, $R_{13}$, $R_{14}$, $R_{15}$ and $R_{16}$ is independently a hydrogen atom, a halogen atom, a cyano group, a hydroxyl group, an amino group, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_2$-$C_{30}$ heteroaryl group or a substituted amino group represented by —N(Z')(Z"); and each of Z' and Z" is independently a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group, or a substituted or unsubstituted $C_5$-$C_{30}$ heterocycloalkyl group.

* * * * *